United States Patent
Tanoue

(10) Patent No.: US 8,790,249 B2
(45) Date of Patent: Jul. 29, 2014

(54) ENDOSCOPE, OPTICAL MEMBER, AND METHOD OF MANUFACTURING ENDOSCOPE

(75) Inventor: Tetsuya Tanoue, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1611 days.

(21) Appl. No.: 11/885,899

(22) PCT Filed: Dec. 22, 2005

(86) PCT No.: PCT/JP2005/023659
§ 371 (c)(1),
(2), (4) Date: Mar. 5, 2009

(87) PCT Pub. No.: WO2006/095490
PCT Pub. Date: Sep. 14, 2006

(65) Prior Publication Data
US 2010/0152540 A1 Jun. 17, 2010

(30) Foreign Application Priority Data
Mar. 8, 2005 (JP) .................................. 2005-064435

(51) Int. Cl.
*A61B 1/04* (2006.01)

(52) U.S. Cl.
USPC .......................................... 600/129; 600/133

(58) Field of Classification Search
CPC ........... A61B 1/00163; A61B 1/00096; A61B 1/042; A61B 1/051; A61B 1/06
USPC ......................................... 600/101, 129, 133
See application file for complete search history.

(56) References Cited

U.S. PATENT DOCUMENTS

| | | | | |
|---|---|---|---|---|
| 5,609,561 | A * | 3/1997 | Uehara et al. | 600/133 |
| 6,695,775 | B2 * | 2/2004 | Watanabe et al. | 600/176 |
| 6,773,392 | B2 * | 8/2004 | Kikuchi et al. | 600/129 |
| 2001/0016679 | A1 | 8/2001 | Futatsugi et al. | |
| 2002/0128535 | A1 | 9/2002 | Kikuchi et al. | |
| 2003/0149339 | A1 * | 8/2003 | Ishibiki | 600/160 |
| 2005/0123816 | A1 * | 6/2005 | Gao et al. | 429/30 |
| 2010/0303722 | A1 * | 12/2010 | Jin et al. | 424/9.1 |
| 2012/0029276 | A1 * | 2/2012 | Baumann et al. | 600/101 |

FOREIGN PATENT DOCUMENTS

| | | |
|---|---|---|
| JP | 04-170929 | 6/1992 |
| JP | 8-170929 | 7/1996 |
| JP | 09-234183 | 9/1997 |
| JP | 2000-135196 | 5/2000 |

(Continued)

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

An endoscope includes a distal end portion body 31 formed of a metal, a distal end portion cover 32 formed of an insulating resin to cover the distal end portion body 31, and a cover lens 25 disposed at a position at which the circumferential surface of the cover lens 25 is contactable with both the distal end portion body 31 and the distal end portion cover 32. In the above, the proximal end side of the circumferential surface of the cover lens 25 is bonded to the distal end portion body 31 by soldering along the circumferential direction. Meanwhile, the distal end side of the circumferential surface of the cover lens 25 is bonded to the distal end portion cover 32 by adhesion along the circumferential direction. Each of bonding surfaces of the cover lens 25 and the distal end portion body 31 is previously formed with a metal film for improving the flow of a liquid solder.

5 Claims, 7 Drawing Sheets

(56) References Cited

FOREIGN PATENT DOCUMENTS

| | | |
|---|---|---|
| JP | 2001-212075 | 8/2001 |
| JP | 2002-085326 | 3/2002 |
| JP | 2002-336190 | 11/2002 |
| JP | 2003-169775 | 6/2003 |
| JP | 2003-220027 | 8/2003 |
| JP | 2003-230534 | 8/2003 |
| JP | 2004-94043 | 3/2004 |

\* cited by examiner

ENDOSCOPE, OPTICAL MEMBER, AND METHOD OF MANUFACTURING ENDOSCOPE

TECHNICAL FIELD

The present invention relates to an endoscope including an optical system in a distal end portion of an insertion section, a method of manufacturing the endoscope, and an optical member which can be disposed in a distal end portion of an insertion section of an endoscope.

BACKGROUND ART

An endoscope has been widely used in such fields as the medical field and the industrial field. In general, the endoscope is configured to include an elongated insertion section which is inserted into the body of a subject. A distal end portion of the insertion section is provided with, for example, an illumination optical system for illuminating an examined site and an observation optical system for forming an image of the examined site illuminated by the illumination optical system. If the endoscope is an optical endoscope, a distal end surface of an image guide is disposed at the imaging position of the observation optical system. Meanwhile, if the endoscope is an electronic endoscope, an image pickup device, such as a CCD, is disposed at the imaging position.

The endoscope is classified into a rigid endoscope and a flexible endoscope in accordance with the flexibility of the insertion section. In the flexible endoscope of the two types of endoscopes, the insertion section has flexibility but includes a distal end portion body formed of a rigid material, such as a metal, for example, in the distal end portion of the insertion section. The distal end portion body is fixed with lenses of the above-described optical systems and lens frames for holding the lenses. Further, a distal end portion cover formed of an insulating resin or the like is attached to the distal end portion body from the distal end side so that the distal end portion body formed of a metal or the like is insulated from the outside.

Conventionally, a variety of proposals have been made on a technique of fixing the lenses of the optical systems to the distal end portion body in the above-described configuration.

For example, paragraph numbers [0069] to [0073] of Japanese Unexamined Patent Application Publication No. 2000-135196 describe a technique of fixing a lens to a lens frame by solder bonding and solder-bonding the lens frame to a distal end portion body. A distal end portion cover is then fixed by bonding to the distal end portion body fixed with the lens and the lens frame.

Meanwhile, a paragraph number [0024] of Japanese Unexamined Patent Application Publication No. 2002-85326 describes a technique of fixing a lens by adhering the lens to a distal end portion body and a distal end portion cover. With reference to FIG. 13, description will now be made of the technique described in the Japanese Unexamined Patent Application Publication No. 2002-85326 by taking an example in which the lens forms an illumination optical system. FIG. 13 is a cross-sectional view illustrating a configuration for fixing a cover lens of the illumination optical system in a conventional example. FIG. 13 shows a cross section cut from the central axis O of the insertion direction in such a direction that the cross section includes the illumination optical system.

A distal end portion body 31 is provided with a through hole 31c, and a light guide 45 forming the illumination optical system is disposed in the through hole 31c. On the distal end side of the light guide 45, a cover lens 25, through which illumination light transmitted through the light guide 45 is expanded forward and emitted, is disposed in a distal end surface 21 to be exposed. The cover lens 25 is bonded to the distal end portion body 31 and a distal end portion cover 32 via an adhesive agent 91. The outer circumferential surface of an insertion section is covered by an outer cover tube 41. The outer cover tube 41 is wound around by a wire 42 on the distal end side thereof and fixed by an adhesive layer 43.

In such a configuration as described in the Japanese Unexamined Patent Application Publication No. 2002-85326 and FIG. 13, the cover lens 25 is bonded to the distal end portion body 31 and the distal end portion cover 32 solely by adhesion, as described above. However, an adhered portion exposed outside of the endoscope is often dipped in chemicals such as disinfectant, so that the portion is sometimes eroded by the chemicals. Therefore, though various kinds of adhesives improved to have high resistance against such chemicals are developed, there is a need for joint means which essentially has resistance against chemicals and is capable of ensuring watertightness.

Meanwhile, in such a configuration as described in the Japanese Unexamined Patent Application Publication No. 2000-135196, the lens frame used to fix the lens includes not only the adhered portion but also the soldered portion. Accordingly, the resistance against chemicals can be ensured by the soldered portion. However, in the art disclosed in the publication, the lens frame is required. Therefore, it is inevitable that the diameter of the distal end portion of the endoscope becomes larger than that in a configuration without the lens frame.

The present invention has been made in view of the above circumstances, and an object of the present invention is to provide an endoscope capable of improving the chemical resistance in the vicinity of an optical member disposed in a distal end portion of the endoscope and enabling a reduction in diameter of the endoscope, a method of manufacturing the endoscope, and an optical member which can be disposed in a distal end portion of an insertion section of the endoscope.

DISCLOSURE OF INVENTION

Means for Solving the Problem

To achieve the above object, an endoscope according to a first aspect of the present invention includes a first member disposed in a distal end portion of an insertion section, a second member disposed in the distal end portion of the insertion section, and an optical member having a surface, at least a portion of which contactably faces the first member, and at least another portion of which contactably faces the second member. The portion of the optical member contactably facing one of the first and second members is bonded to the one of the first and second members by metal welding. Meanwhile, the portion of the optical member contactably facing the other one of the first and second members is bonded to the other one of the first and second members by adhesion.

An endoscope according to a second aspect of the present invention is the endoscope according to the first aspect, in which at least a portion of the optical member may be exposed to the outside of the endoscope.

An endoscope according to a third aspect of the present invention is the endoscope according to the second aspect, in which the first member may be a distal end portion body formed of a rigid material, and the second member may be a distal end portion cover formed of an insulating material to cover the distal end portion body.

An endoscope according to a fourth aspect of the present invention is the endoscope according to the first aspect, in which the metal welding for bonding the optical member to the one of the first and second members may be soldering.

An endoscope according to a fifth aspect of the present invention is the endoscope according to the fourth aspect, in which the surface of the optical member bonded to the one of the first and second members may be formed with a metal film for improving the flow of a liquid solder, and the surface of the one of the first and second members bonded to the optical member may be formed with a metal film for improving the flow of the liquid solder.

An endoscope according to a sixth aspect of the present invention is the endoscope according to the fifth aspect, in which the metal film formed on the surface of the optical member may be configured to include a Cr metal film having a thickness of 0.05 to 0.5 μm, a Ni metal film having a thickness of 0.6 to 3 μm laminated on the Cr metal film, and an Au metal film having a thickness of 0.1 to 1 μm laminated on the Ni metal film, and the metal film formed on the surface of the one of the first and second members may be configured to include a Ni metal film having a thickness of 1 to 6 μm and an Au metal film having a thickness of 0.06 to 0.6 μm laminated on the Ni metal film.

An optical member according to a seventh aspect of the present invention is disposed in a distal end portion of an insertion section of an endoscope which includes a first member and a second member, with at least a portion of the surface of the optical member contactably facing the first member, and at least another portion of the surface of the optical member contactably facing the second member. Only the portion of the optical member contactably facing one of the first and second members is formed with a metal film for improving the flow of a liquid solder.

An optical member according to an eighth aspect of the present invention is the optical member according to the seventh aspect, in which the metal film may be configured to include a Cr metal film having a thickness of 0.05 to 0.5 μm, a Ni metal film having a thickness of 0.6 to 3 μm laminated on the Cr metal film, and an Au metal film having a thickness of 0.1 to 1 μm laminated on the Ni metal film.

A method of manufacturing an endoscope according to a ninth aspect of the present invention includes the steps of bonding the entire circumference on the proximal end side of the circumferential surface of an optical member to a distal end portion body with the use of a solder, attaching a distal end portion cover from the distal end side, and fixing the distal end portion cover to the distal end portion body and the optical member with the use of an adhesive agent.

BEST MODE FOR CARRYING OUT THE INVENTION

An embodiment of the present invention will be described below with reference to the drawings.

First Embodiment

Figure 1:
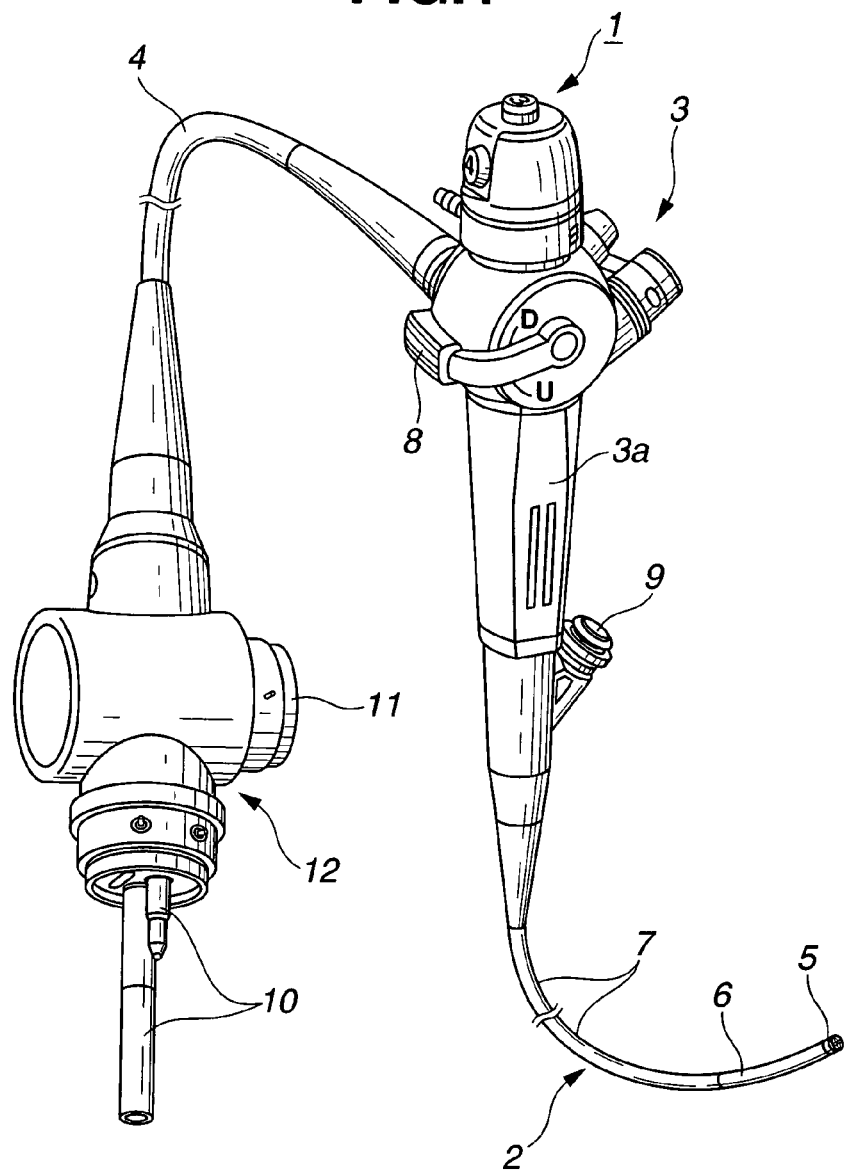
FIG. 1 is a perspective view illustrating the exterior of an endoscope in a first embodiment of the present invention.
Figure 2:
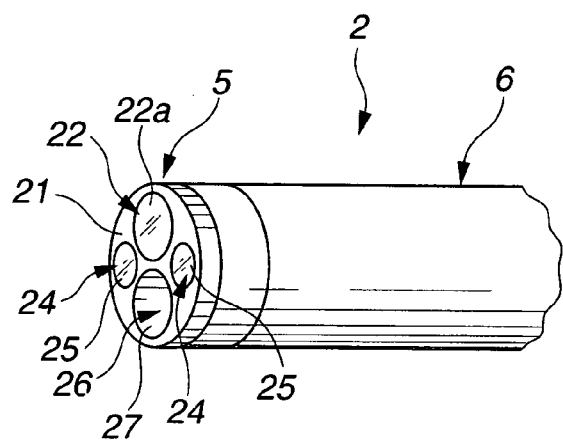
FIG. 2 is an enlarged perspective view of essential parts, illustrating a distal end surface side of a distal end portion of an insertion section in the first embodiment.
Figure 3:
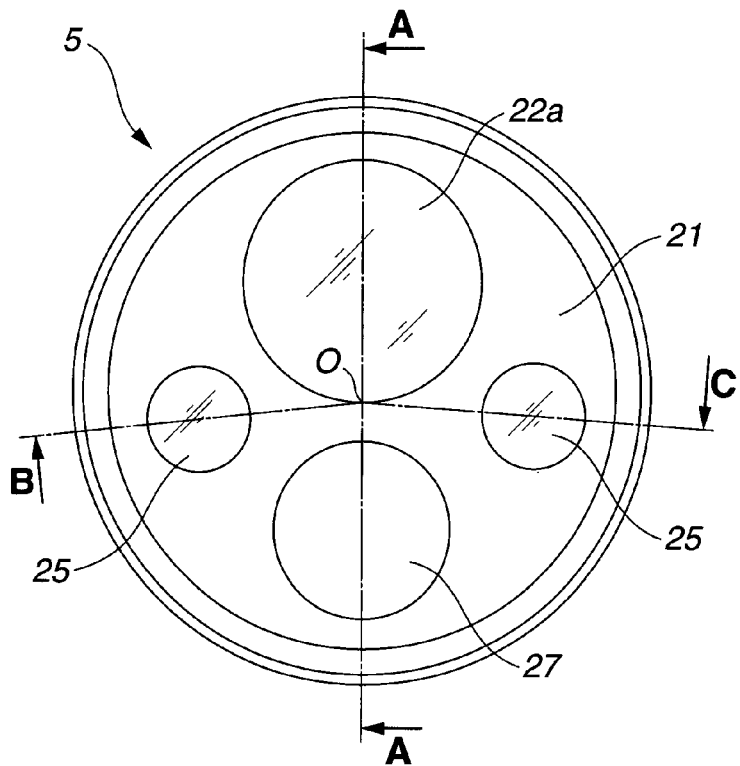
FIG. 3 is a front view illustrating a configuration of the distal end surface of the distal end portion of the insertion section in the first embodiment.
Figure 4:
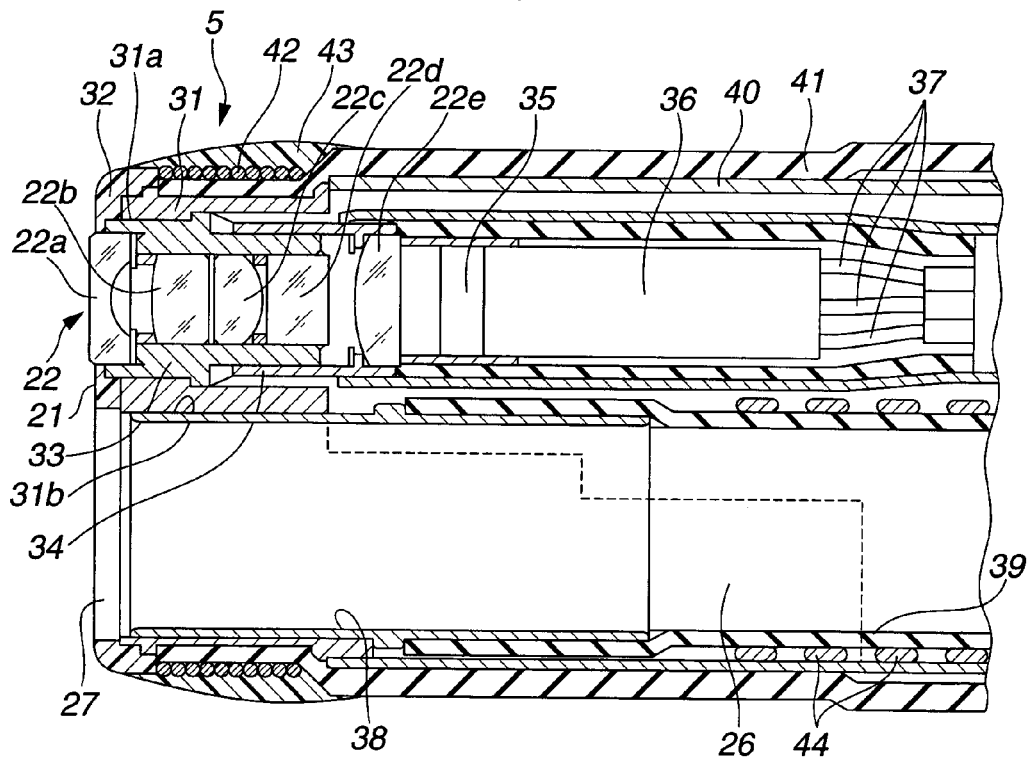
FIG. 4 is a cross-sectional view along the A-A line, illustrating a portion inside the distal end portion of the insertion section in the first embodiment, which includes a forceps channel and an observation optical system.
Figure 5:
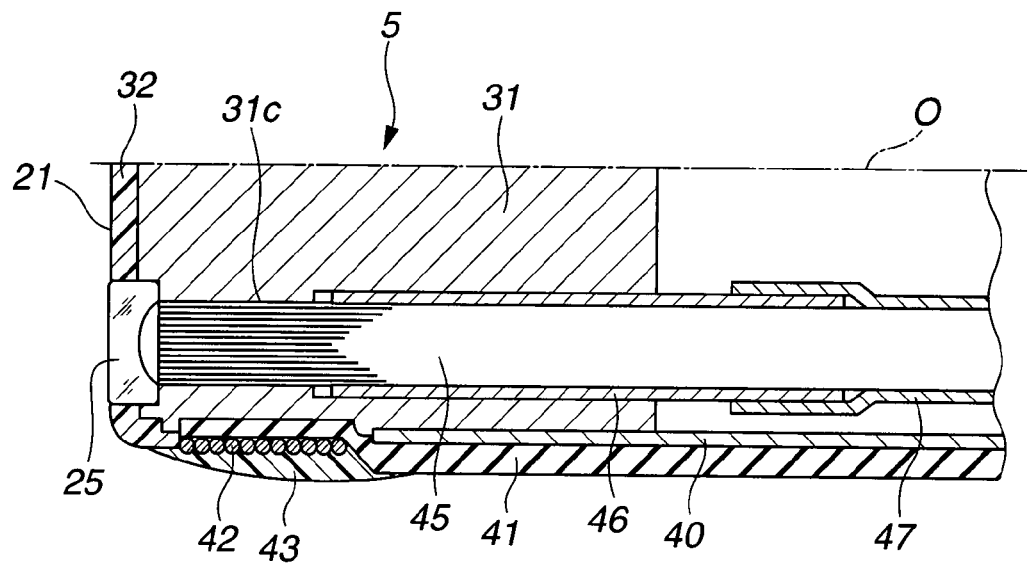
FIG. 5 is a cross-sectional view along the O-B line or the O-C line, illustrating a portion inside the distal end portion of the insertion section in the first embodiment, which includes an illumination optical system.
Figure 6:
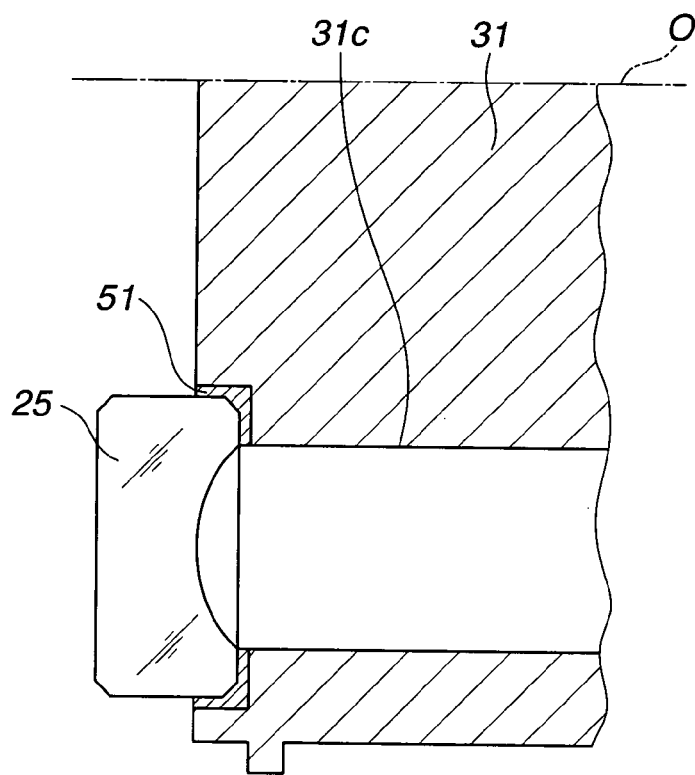
FIG. 6 is a cross-sectional view illustrating a configuration of the first embodiment, in which a distal end portion body is attached with a cover lens.
Figure 7:
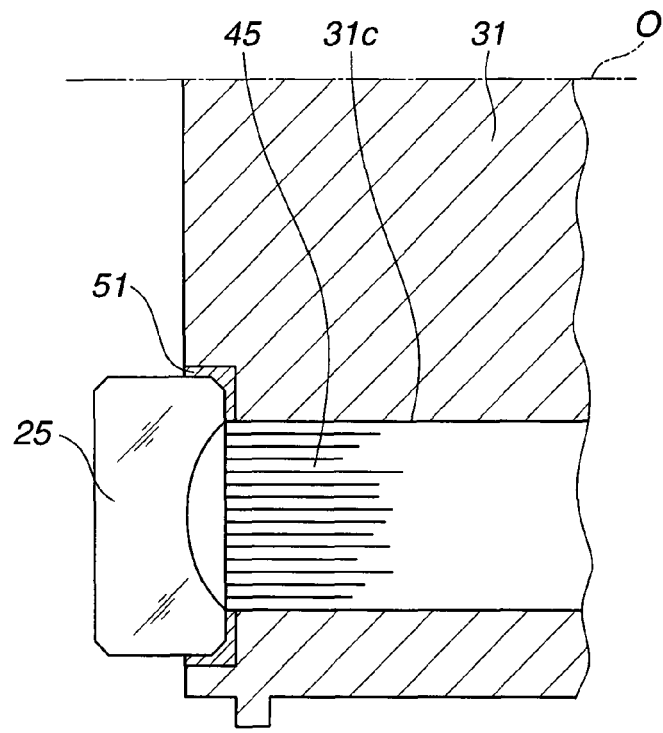
FIG. 7 is a cross-sectional view illustrating a configuration of the first embodiment, in which the distal end portion body is attached with the cover lens and a light guide.
Figure 8:
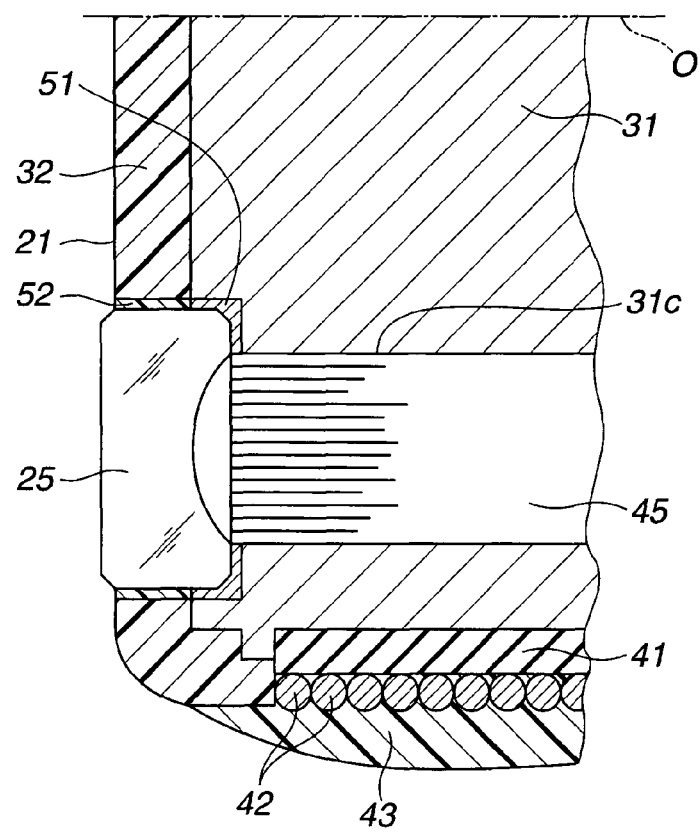
FIG. 8 is a cross-sectional view illustrating a configuration of the first embodiment, in which the distal end portion body and the cover lens are further attached with a distal end portion cover and other members.
Figure 9:
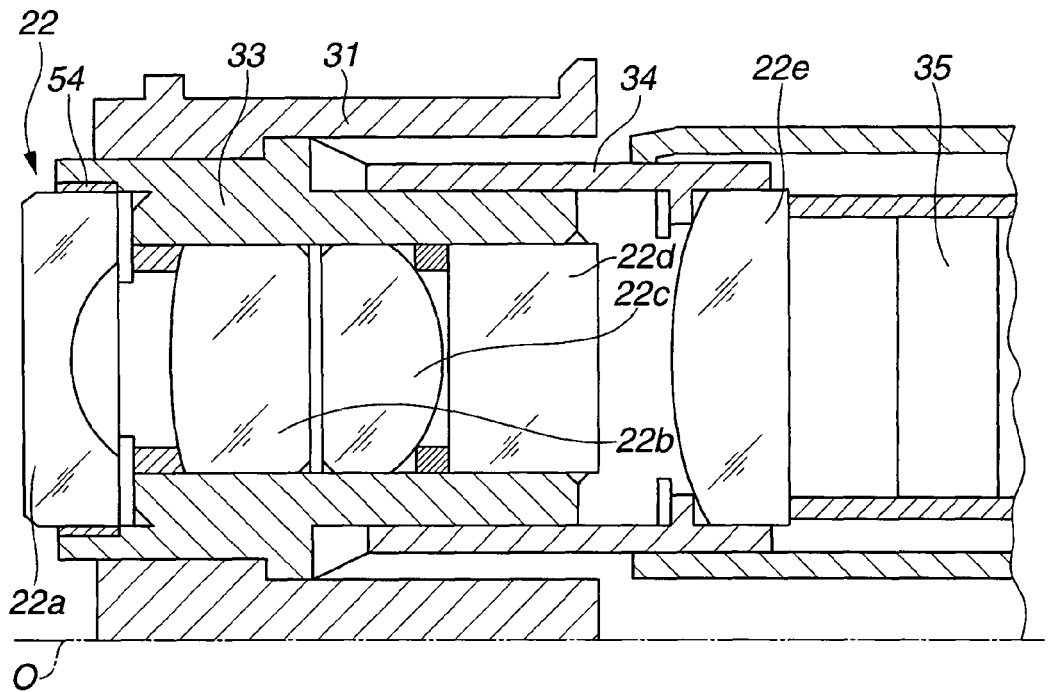
FIG. 9 is a cross-sectional view illustrating a state of the first embodiment, in which a lens supporting member and the distal end portion body are attached with the observation optical system and a CCD.
Figure 10:
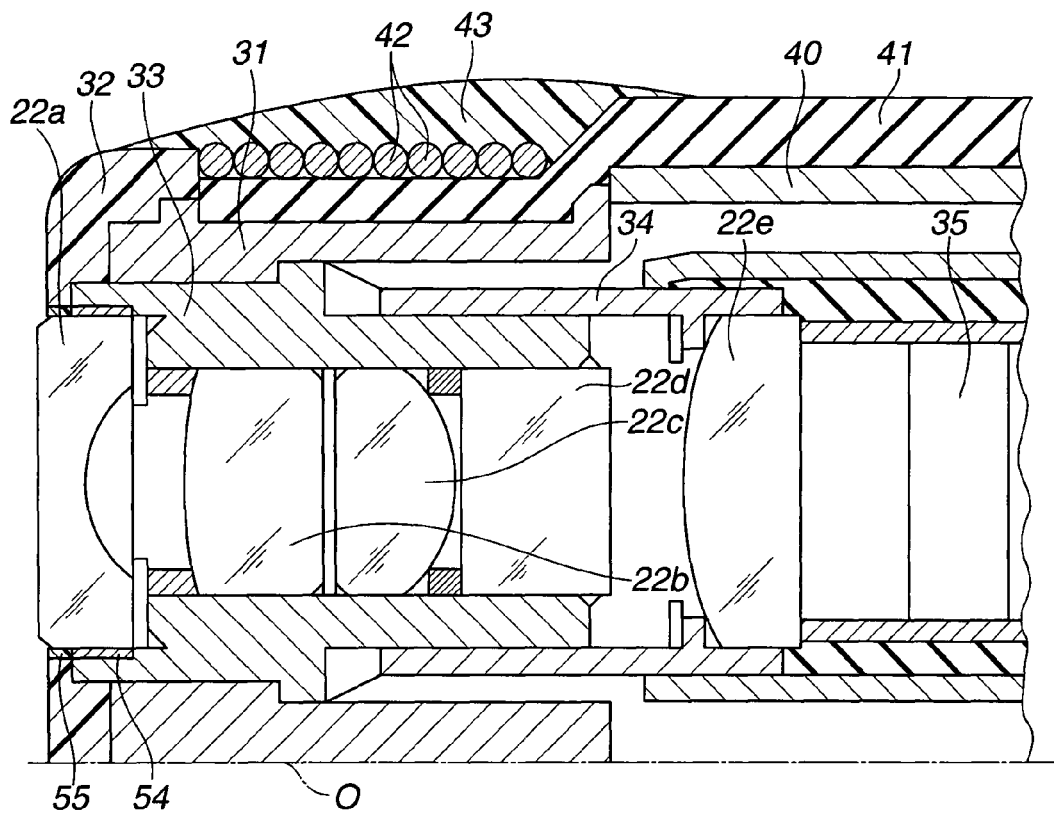
FIG. 10 is a cross-sectional view illustrating a configuration of the first embodiment, in which the lens supporting member, the distal end portion body, the observation optical system, and the CCD are further attached with the distal end portion cover and other members.
Figure 11:
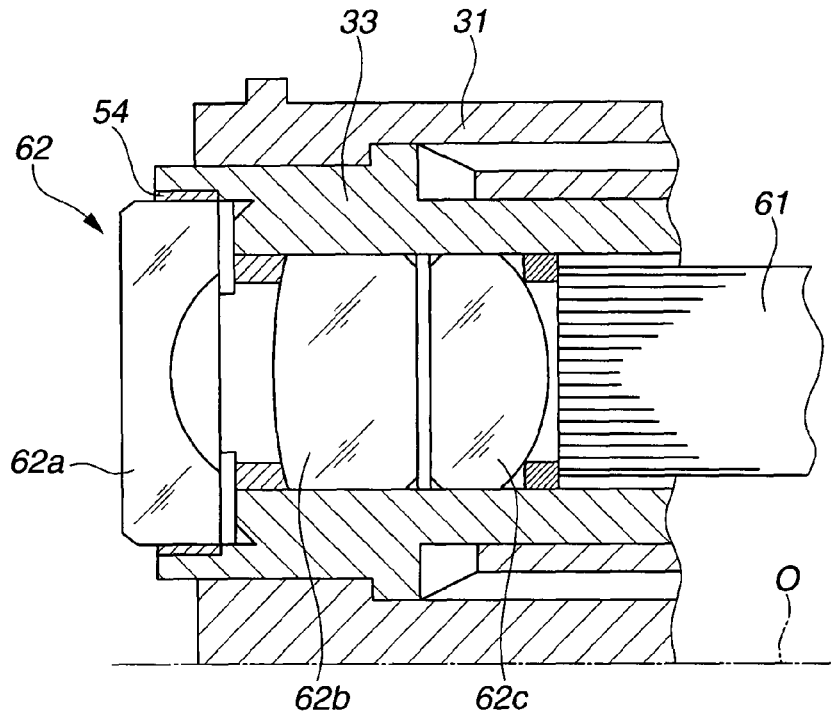
FIG. 11 is a cross-sectional view illustrating a state of the first embodiment, in which the lens supporting member and the distal end portion body are attached with the observation optical system and an image guide.
Figure 12:
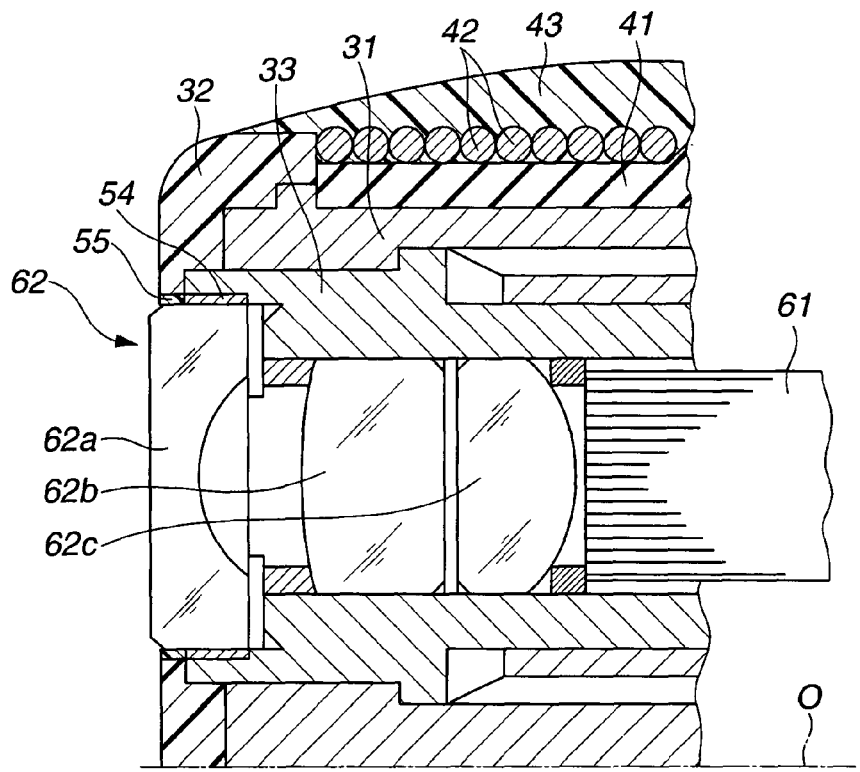
FIG. 12 is a cross-sectional view illustrating a configuration of the first embodiment, in which the lens supporting member, the distal end portion body, the observation optical system, and the image guide are further attached with the distal end portion cover and other members.
Figure 13:
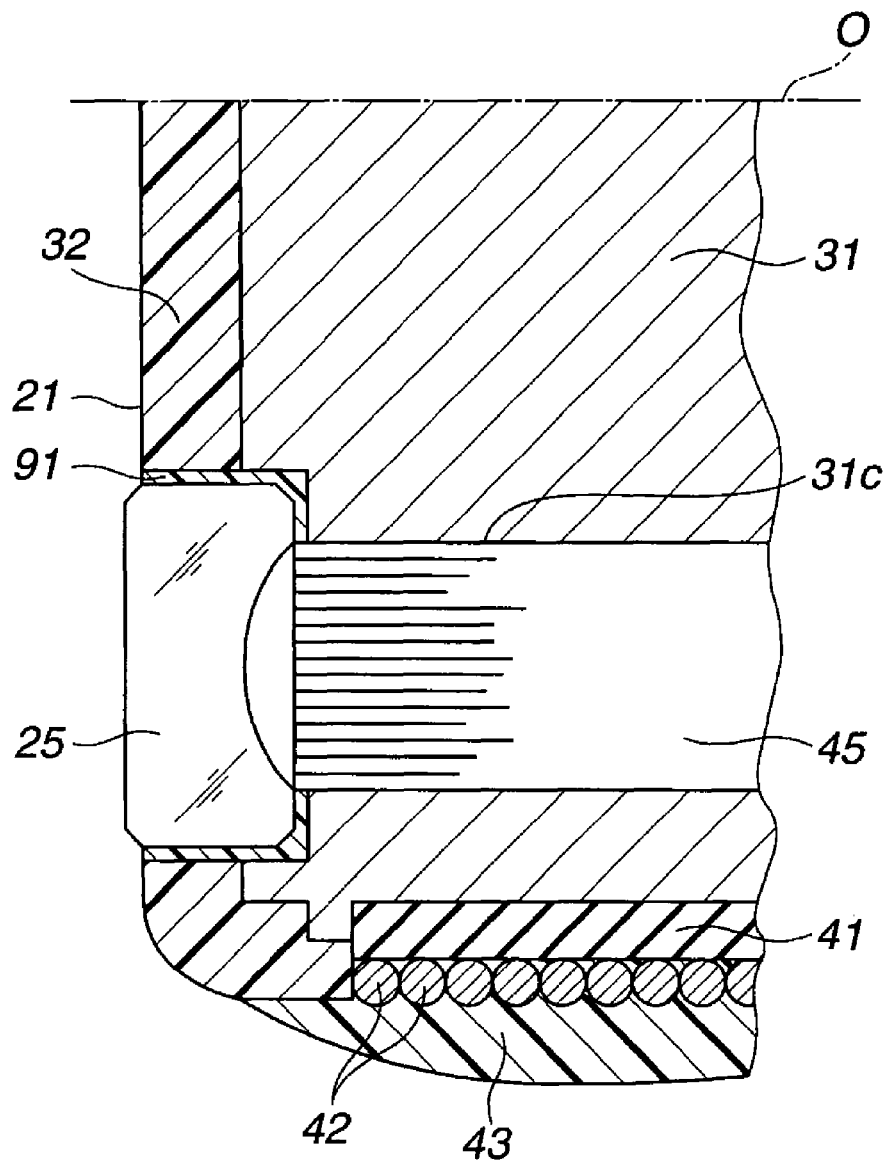
FIG. 13 is a cross-sectional view illustrating a configuration of a conventional example for fixing a cover lens of an illumination optical system.

FIG. 1 through FIG. 12 show a first embodiment of the present embodiment. FIG. 1 is a perspective view illustrating the exterior of an endoscope. FIG. 2 is an enlarged perspective view of essential parts, illustrating a distal end surface side of a distal end portion of an insertion section. FIG. 3 is a front view illustrating a configuration of the distal end surface of the distal end portion of the insertion section. FIG. 4 is a cross-sectional view along the A-A line, illustrating a portion inside the distal end portion of the insertion section including a forceps channel and an observation optical system. FIG. 5 is a cross-sectional view along the O-B line or the O-C line, illustrating a portion inside the distal end portion of the insertion section including an illumination optical system. FIG. 6 is a cross-sectional view illustrating a configuration in which a distal end portion body is attached with a cover lens. FIG. 7 is a cross-sectional view illustrating a configuration in which the distal end portion body is attached with the cover lens and a light guide. FIG. 8 is a cross-sectional view illustrating a configuration in which the distal end portion body and the cover lens are further attached with a distal end portion cover and other members. FIG. 9 is a cross-sectional view illustrating a state in which a lens supporting member and the distal end portion body are attached with the observation optical system and a CCD. FIG. 10 is a cross-sectional view illustrating a configuration in which the lens supporting member, the distal end portion body, the observation optical system, and the CCD are further attached with the distal end portion cover and other members. FIG. 11 is a cross-sectional view illustrating a state in which the lens supporting member and the distal end portion body are attached with the observation optical system and an image guide. FIG. 12 is a cross-sectional view illustrating a configuration in which the lens supporting member, the distal end portion body, the observation optical system, and the image guide are further attached with the distal end portion cover and other members.

In the present embodiment, a medical electronic endoscope configured to include an image pickup device at the imaging position of an observation optical system will be described as an example of the endoscope.

As illustrated in FIG. 1, an endoscope 1 includes an elongated insertion section 2 inserted into a body cavity, an operation section 3 provided on the proximal end side of the insertion section 2, and a connector cord (alternatively referred to as a universal cord) 4 extending from the operation section 3.

The insertion section 2 is configured to include a distal end portion 5, a bendable bending portion 6, and a long flexible tube portion 7 having flexibility, which are disposed in this order from the distal end side to the proximal end side.

The operation section 3 is provided with a grasping portion 3a gripped by a surgeon. Further, at the rear position of the grasping portion 3a of the operation section 3 in relation to the surgeon, a bending operation lever 8 is provided which is used to perform an operation of bending the bending portion 6. The bending operation lever 8 is fixed with one end of a not-illustrated operation wire inserted through the insertion section 2, and the other end of the operation wire is fixed to the distal end of the bending portion 6. Therefore, when the surgeon pulls the operation wire by operating the bending operation lever 8, the bending portion 6 is bent up and down. Thereby, the distal end portion 5 can be directed in a desired direction through the operation of the bending operation lever 8.

Further, the front side of the grasping portion 3a of the operation section 3 in relation to the surgeon is provided with a forceps insertion opening 9 through which a treatment instrument, such as a forceps, is inserted. The treatment instrument inserted from the forceps insertion opening 9 is inserted into a forceps channel 26 (see FIGS. 2 and 4) provided inside the insertion section 2, and projects from a forceps opening 27 (see FIGS. 2, 3, and 4) which forms an opening of the distal end portion 5. If the treatment instrument is operated in the above state, the procedure of collecting tissue from an affected area can be performed, for example.

Meanwhile, a distal end portion of the connector cord 4 extending from the operation section 3 is provided with a connector 12 which includes a light source connecting portion 10 and an image processor connecting portion 11.

The light source connecting portion 10 provided on the distal end side of the connector 12 is configured to include, for example, a light guide connector for connecting one end of a light guide 45 (see FIG. 5) inserted through the insertion section 2, the operation section 3, and the connector cord 4. Further, the light source connecting portion 10 is attachably and detachably connected to a not-illustrated light source device. In a state in which the light source connecting portion 10 is connected to the light source device, illumination light emitted from the light source device is transmitted to the light guide 45 through the light source connecting portion 10, and then is transmitted by the light guide 45 to the distal end side of the insertion section 2.

Meanwhile, the image processor connecting portion 11 provided to a side portion of the connector 12 is a connecting portion for connecting the endoscope 1 to a not-illustrated image processor, such as a video processor. A video signal sent from a later-described CCD 35 (see FIG. 4) disposed in the distal end portion 5 is transmitted to the image processor through the image processor connecting portion 11, processed in the image processor, and displayed on a monitor or the like connected to the image processor.

As illustrated in FIGS. 2 and 3, in a distal end surface 21 of the distal end portion 5 of the insertion section 2, there are exposed a first lens 22a of an observation optical system 22 which forms an optical image of an examined site on the later-described CCD 35, cover lenses 25 for covering distal end portions of illumination optical systems 24 which illuminate the examined site, and the forceps opening 27 which forms an opening on the exit side of the forceps channel 26 communicating with the forceps insertion opening 9.

As illustrated in FIGS. 4 and 5, the distal end portion 5 includes a distal end portion body 31, which forms a first member formed of a rigid material, such as a metal, for example, into a substantially cylindrical shape. The interior of the distal end portion body 31 is formed with a through hole 31a which extends along the insertion direction and in which the observation optical system 22 is disposed, a through hole 31b which extends along the insertion direction and in which the forceps channel 26 is disposed, and two through holes 31c which extend along the insertion direction and in which the respective illumination optical systems 24 are disposed.

The observation optical system 22 disposed in the through hole 31a is attached to the through hole 31a in a state in which the observation optical system 22 is supported by lens supporting members 33 and 34, which form the first member.

The observation optical system 22 is configured to include the first lens 22a, a second lens 22b, a third lens 22c, a fourth lens 22d, and a fifth lens 22e, which are disposed in this order from the distal end side toward the proximal end side.

Among the above lenses, the first to fourth lenses 22a to 22d are fixed to the lens supporting member 33, which is a frame body formed of a rigid material, such as a metal, for example, into a cylindrical shape. As described above, the lens supporting member 33 is attached to the distal end portion body 31 and fixed thereto by soldering or adhesion. Meanwhile, the fifth lens 22e is somewhat large in diameter, and thus is fixed to the second lens supporting member 34, which is fit to the outside of a proximal end side portion of the lens supporting member 33.

At the imaging position of the above-described observation optical system 22, an image pickup surface of the CCD (Charge Coupled Device) 35 serving as an image pickup device is disposed to convert the formed optical image into an electrical signal. The CCD 35 is mounted on an electrical circuit board 36. From the electrical circuit board 36, signal lines 37 extend to be connected to the above-described image processor connecting portion 11 through the insertion section 2, the operation section 3, and the connector cord 4.

Further, in the through hole 31b, a distal-end-side forceps base 38 is fixed to the inside of the through hole 31b by soldering or adhesion, for example, and a hollow and flexible channel tube 39 is inserted in through hole 31b and fixed to the outside of a proximal end side portion of the distal-end-side forceps base 38 by an adhesive agent or the like. Further, a helical channel coil 44 formed of a metal is fit to the outer circumference of a bending portion of the channel tube 39 to fulfill such functions as preventing buckling of the channel tube 39, improving the bending resistance of the channel tube 39, and reducing the amount of operation of the channel tube 39.

Further, as illustrated in FIG. 5, the light guide 45 formed by a fiber bundle is inserted in each of the through holes 31c, and the cover lens 25 is attached to a diameter-expanded portion on the distal end side of the through hole 31c by a structure which will be later described in details. FIG. 5 illustrates a cross section cut from the central axis O of the insertion direction in such a direction that the cross section includes an illumination optical system (i.e., the cross section along the O-B line or the O-C line in FIG. 3). A proximal end side portion of the light guide 45 in the through hole 31c is covered by a protective tube 46, and a tube 47 for covering the light guide 45 is externally inserted over a proximal end side portion of the protective tube 46. The light guide 45 is connected to the above-described light source connecting portion 10 through the insertion section 2, the operation section 3, and the connector cord 4. Thereby, the illumination light emitted from the light source device is guided to the distal end portion 5 by the light guide 45. Thereafter, the illumination light emitted from a distal end surface of the light guide 45 is expanded forward and emitted through the cover lens 25 to illuminate the examined site.

The distal end portion cover 32, which forms a second member, is attached to the distal end side of the above-described distal end portion body 31 by adhesion or the like, for example. The distal end portion cover 32 is formed of a material of insulating resin having good autoclave resistance. Specifically, the material includes, for example, polyphenylsulfone, polysulfone, and so forth.

Further, a first joint ring 40 forming the most distal end of the bending portion 6 is fit to the outside of a proximal end side portion of the distal end portion body 31. Then, the outer cover tube 41, which is watertight and airtight and has flexibility, externally covers the entirety of the distal end portion body 31 and the bending portion 6 including the first joint ring 40.

A distal end portion of the outer cover tube 41 is fixed to the distal end portion body 31, with a wire 42 wound around the distal end portion of the outer cover tube 41 outside a portion of the distal end portion body 31 on the proximal end side from the distal end portion cover 32. Further, an adhesive layer 43 formed of an adhesive agent or the like is formed to cover the wire 42. The adhesive layer 43 is formed into a sufficient thickness to cover a range from the surface of the distal end portion cover 32 to the surface of the outer cover tube 41, to thereby achieve a configuration endurable against the erosion by chemicals and so forth. Accordingly, sufficient watertightness and airtightness are maintained in the side surface of the distal end portion 5 of the insertion section 2.

With reference to FIGS. 6 to 8, description will now be made of a connecting structure for connecting the cover lens 25 of the illumination optical system 24, the distal end portion body 31, and the distal end portion cover 32.

As illustrated in FIG. 6, the cover lens 25 is first bonded to the distal end portion body 31 with the use of a solder 51 in the entire circumference on the proximal end side of the circumferential surface of the cover lens 25.

That is, the cover lens 25 is an optical member formed of a glass material into a substantially short cylindrical shape having an optical surface. A proximal end side portion of the outer circumferential surface of the cover lens 25 is formed with a metal film for reducing the contact angle with respect to the liquid solder (i.e., for improving the flow of the solder). Specifically, the metal film is configured to include, for example, a Cr metal film having a thickness of 0.05 to 0.5 μm, a Ni metal film having a thickness of 0.6 to 3 μM laminated on the Cr metal film, and an Au metal film having a thickness of 0.1 to 1 μm laminated on the Ni metal film.

Similarly, the inner circumferential surface of the diameter-expanded portion of the through hole 31c of the distal end portion body 31, i.e., the inner circumferential surface of a portion of the through hole 31c in contact with the cover lens 25 is formed with a metal film for reducing the contact angle with respect to the liquid solder (i.e., for improving the flow of the solder). Specifically, the metal film is configured to include, for example, a Ni metal film having a thickness of 1 to 6 μm and an Au metal film having a thickness of 0.06 to 0.6 μm laminated on the Ni metal film.

The metal films of the cover lens 25 and the distal end portion body 31 are formed by sputtering, for example.

As the solder 51, an Au—Sn solder (e.g., an Au80-Sn20 solder or an Au10-Sn90 solder) is used. With the use of the solder not including lead, therefore, an environmentally conscious configuration is obtained. Due to the action of the above-described metal films, the solder 51 substantially evenly flows over the entire circumference of the circumferential surfaces on which the cover lens 25 and the distal end portion body 31 come in contact with each other, to thereby bond the cover lens 25 to the distal end portion body 31 while maintaining the watertightness and the airtightness.

Thereafter, as illustrated in FIG. 7, the light guide 45 is inserted into the through hole 31c to a predetermined position and fixed thereto.

Then, as illustrated in FIG. 8, the distal end portion cover 32 is attached from the distal end side and fixed to the distal end portion body 31 and the cover lens 25 by an adhesive agent. Thereby, as illustrated in FIG. 8, a ring-shaped layer of the adhesive agent 52 is formed between the cover lens 25 and the distal end portion cover 32.

Thereafter, as described above, the outer cover tube 41 is attached, the wire 42 is wound, and the adhesive layer 43 is formed.

Thereby, the circumferential surface of the cover lens 25, i.e., an optical lens is directly bonded to the other members by two types of measures, i.e., the soldering and the adhesion, without the interposition of a lens frame and so forth.

Subsequently, with reference to FIGS. 9 and 10, description will be made of a connecting structure for connecting the first lens 22a of the observation optical system 22, the lens supporting member 33, and the distal end portion cover 32.

As described above, the lens supporting member 33 is attached with the first to fourth lenses 22a to 22d. Among the lenses, the first lens 22a located on the most distal end side is bonded to the lens supporting member 33 with the use of a solder 54 in the entire circumference on the proximal end side of the circumferential surface of the first lens 22a.

The first lens 22a herein is an optical member formed of a glass material into a substantially short cylindrical shape having an optical surface. A proximal end side portion of the outer circumferential surface of the first lens 22a is formed with a metal film for reducing the contact angle with respect to the liquid solder (i.e., for improving the flow of the solder). Similarly as in the foregoing description, a specific example of the metal film includes a Cr metal film having a thickness of 0.05 to 0.5 μm, a Ni metal film having a thickness of 0.6 to 3 μm laminated on the Cr metal film, and an Au metal film having a thickness of 0.1 to 1 μm laminated on the Ni metal film.

Similarly, the inner circumferential surface of a distal end side portion of the lens supporting member 33, i.e., the inner circumferential surface of a portion of the lens supporting member 33 in contact with the first lens 22a is formed with a metal film for reducing the contact angle with respect to the liquid solder (i.e., for improving the flow of the solder). Similarly as in the foregoing description, a specific example of the metal film includes a Ni metal film having a thickness of 1 to 6 μm and an Au metal film having a thickness of 0.06 to 0.6 μm laminated on the Ni metal film.

The metal films of the first lens 22a and the lens supporting member 33 are similarly formed by sputtering, for example.

As the solder 54, an Au—Sn solder (e.g., an Au80-Sn20 solder or an Au10-Sn90 solder) is used, similarly as in the foregoing description.

Then, as illustrated in FIG. 10, the distal end portion cover 32 is attached from the distal end side and fixed to the lens supporting member 33, the distal end portion body 31, and the first lens 22a by an adhesive agent. Thereby, as illustrated in FIG. 10, a ring-shaped layer of the adhesive agent 55 is formed between the first lens 22a and the distal end portion cover 32.

Further, the outer cover tube 41 is attached, the wire 42 is wound, and the adhesive layer 43 is formed, similarly as in the foregoing description.

With reference to FIGS. 11 and 12, description will now be made of an example in which the endoscope is an optical endoscope.

It is now assumed that an observation optical system 62 of the optical endoscope is configured to include, for example, a first lens 62a, a second lens 62b, and a third lens 62c, as optical members.

In the optical endoscope, a distal end surface of an image guide 61 formed by a fiber bundle is disposed at the position of the imaging surface of the observation optical system 62.

Similarly as in the case of the above-described electronic endoscope, the first lens 62a of the observation optical system 62 is bonded to the lens supporting member 33 with the use of the solder 54 in the entire circumference on the proximal end side of the circumferential surface of the first lens 62a.

At this time, a proximal end side portion of the outer circumferential surface of the first lens 62a is formed with a metal film for reducing the contact angle with respect to the liquid solder (i.e., for improving the flow of the solder), and the inner circumferential surface of a distal end side portion of the lens supporting member 33 is formed with a metal film for reducing the contact angle with respect to the liquid solder (i.e., for improving the flow of the solder), similarly as in the foregoing description.

Thereafter, as illustrated in FIG. 12, the distal end portion cover 32 is attached from the distal end side and fixed to the lens supporting member 33, the distal end portion body 31, and the first lens 62a by the adhesive agent. Thereby, as illustrated in FIG. 12, a ring-shaped layer of the adhesive agent 55 is formed between the first lens 62a and the distal end portion cover 32.

Further, the outer cover tube 41 is attached, the wire 42 is wound, and the adhesive layer 43 is formed, similarly as in the foregoing description.

In the above description, while the optical lens located on the most distal end of the illumination optical system is bonded to the distal end portion body by soldering, the optical lens located on the most distal end of the observation optical system is attached to the distal end portion body via the lens supporting member. However, the configuration is not limited to the above. Thus, the optical lens located on the most distal end of the observation optical system may also be bonded directly to the distal end portion body by soldering. Thereby, the lens supporting member becomes unnecessary, and a further reduction in diameter of the endoscope can be achieved.

Further, in the above description, the solder bonding is taken as an example. However, a technique of directly fusing the metals together may be alternatively used. Thus, metal welding in a broad sense including the solder bonding can be employed.

Further, the optical member is not limited to the optical lens, and thus may be a cover glass or another optical member.

Further, the method of bonding the surface of an optical member to other members by two types of measures, i.e., the metal welding and the adhesion is not applied only to the optical member, at least a portion of which is exposed to the outside of the endoscope. Thus, the method can also be applied to the optical member disposed inside the endoscope.

According to the first embodiment as described above, in the optical lens located on the most distal end side of the optical system, such as the illumination optical system and the observation optical system, (i.e., the optical member, at least a portion of which is exposed to the outside of the endoscope), a portion in the axial direction of the circumferential surface of the optical lens is metal-welded (e.g., solder-bonded) over the entire circumference of the portion, while another portion in the axial direction of the circumferential surface of the optical lens is adhered. Due to the metal welding, therefore, the chemical resistance can be improved in the vicinity of the optical lens.

Further, with the use of the advanced technique of bonding an optical member by two types of measures, the optical member can be simultaneously bonded to two different members. Further, the technique can be applied to reduce the diameter of the endoscope. In fact, in the illumination optical system, the optical lens located on the most distal end is soldered to the distal end portion body without the interposition of a lens frame and so forth, and is also adhered to the distal end portion cover. Accordingly, the diameter of the endoscope can be reduced.

Further, in the case in which the optical lens located on the most distal end of the observation optical system is directly soldered to the distal end portion body and directly adhered to the distal end portion cover, the diameter of the endoscope can be further reduced.

Needless to say, the present invention is not limited to the above-described embodiment, and a variety of modifications and applications can be made within a scope not departing from the gist of the invention.

The invention claimed is:

1. An endoscope comprising:
    a distal end portion body disposed in a distal end portion of an insertion section and formed of a rigid material, wherein the distal end portion body defines a first through hole and a second through hole different from the first through hole;
    a distal end portion cover for covering the distal end portion body, the distal end portion cover being disposed in the distal end portion of the insertion section and formed of an insulating material; and
    an optical member arranged to a distal end side of the first through hole of the distal end portion body,
        wherein the optical member has a circumferential surface,
        wherein at least a portion of the optical member is exposed outside of the endoscope,
        wherein an entire circumference of a proximal end side portion of the circumferential surface in an axial direction of the optical member contactably faces the distal end portion body,
        wherein a distal end side portion of the circumferential surface in the axial direction of the optical member contactably faces the distal end portion cover, and wherein the proximal end side portion of the circumferential surface contactably facing the distal end portion body is bonded to the distal end portion body by metal welding, and the distal end side portion of the circumferential surface contactably facing the distal end portion cover is bonded to the distal end portion cover by adhesion.

2. The endoscope according to claim 1, wherein the metal welding for bonding the optical member to the distal end portion body is soldering.

3. The endoscope according to claim 2,
wherein the surface of the optical member bonded to the distal end portion body is formed with a metal film for improving the flow of a liquid solder, and
wherein the surface of the distal end portion body bonded to the optical member is formed with a metal film for improving the flow of the liquid solder.

4. The endoscope according to claim 3,
wherein the metal film formed on the surface of the optical member is configured to include a Cr metal film having a thickness of 0.05 to 0.5 μm, a Ni metal film having a thickness of 0.6 to 3 μm laminated on the Cr metal film, and an Au metal film having a thickness of 0.1 to 1 μm laminated on the Ni metal film, and
wherein the metal film formed on the distal end portion body is configured to include a Ni metal film having a thickness of 1 to 6 μm and an Au metal film having a thickness of 0.06 to 0.6 μm laminated on the Ni metal film.

5. A method of manufacturing an endoscope, the method comprising the steps of:
bonding an entire circumference of a proximal end side portion of a circumferential surface of an optical member to a distal end portion body with the use of a solder, at least a portion of the optical member being exposed outside of the endoscope and the distal end portion body being formed of a rigid material, wherein the distal end portion body defines a first through hole and a second through hole different from the first through hole, and wherein the optical member is arranged to a distal end side of the first through hole of the distal end portion body,
attaching a distal end portion cover from a distal end side of the endoscope, the distal end portion cover formed of an insulating material to cover the distal end portion body; and
fixing the distal end portion cover to the distal end portion body using an adhesive agent and fixing the distal end portion cover to a distal end side portion of the circumferential surface of the optical member using an adhesive agent.

* * * * *